(12) United States Patent
Wang et al.

(10) Patent No.: US 11,577,218 B2
(45) Date of Patent: Feb. 14, 2023

(54) HIGH-LOADING AND ALKALI-RESISTANT PROTEIN A MAGNETIC BEAD AND METHOD OF USE THEREOF

(71) Applicant: Nanjing GenScript Biotech Co., Ltd., Nanjing (CN)

(72) Inventors: Chao Wang, Nanjing (CN); Ruina He, Nanjing (CN); Weijuan Han, Nanjing (CN); Hong Qian, Nanjing (CN); Tao Bai, Nanjing (CN)

(73) Assignee: Nanjing GenScript Biotech Co., Ltd., Nanjing (CN)

( * ) Notice: Subject to any disclaimer, the term of this patent is extended or adjusted under 35 U.S.C. 154(b) by 853 days.

(21) Appl. No.: 16/475,784

(22) PCT Filed: Jan. 4, 2018

(86) PCT No.: PCT/CN2018/071397
§ 371 (c)(1),
(2) Date: Jul. 3, 2019

(87) PCT Pub. No.: WO2018/127099
PCT Pub. Date: Jul. 12, 2018

(65) Prior Publication Data
US 2019/0329218 A1    Oct. 31, 2019

(30) Foreign Application Priority Data
Jan. 4, 2017 (CN) .......................... 201710005878.8

(51) Int. Cl.
*B01J 20/24* (2006.01)
*B01J 20/02* (2006.01)
(Continued)

(52) U.S. Cl.
CPC .......... *B01J 20/24* (2013.01); *B01J 20/0229* (2013.01); *B01J 20/103* (2013.01);
(Continued)

(58) Field of Classification Search
None
See application file for complete search history.

(56) References Cited

U.S. PATENT DOCUMENTS

2016/0237124 A1*  8/2016  Qian ...................... C07K 16/00
2017/0356902 A1   12/2017  Ukekawa

FOREIGN PATENT DOCUMENTS

CN        101143888 A       3/2008
CN        103007846 A       4/2013
(Continued)

OTHER PUBLICATIONS

Jinggang ("Fe3O4 Magnetic Dextran Nanoparticles Modified with SPA Ligand for IgG Purification" Biotechnology Bulletin, 2014, 201-208). (Year: 2014).*

(Continued)

*Primary Examiner* — Clare M Perrin
(74) *Attorney, Agent, or Firm* — Klarquist Sparkman, LLP

(57) ABSTRACT

Provided is a high-loading and alkali-resistant protein A magnetic bead. The magnetic bead can maintain chemical stability under pH 2-14 and has an immunoglobulin G (IgG) binding capacity greater than 50 mg/mL. Further provided is a method for purifying and/or detecting an immunoglobulin, comprising a step of contacting a sample containing the immunoglobulin with the high-loading and alkali-resistant protein A magnetic bead. The alkali-resistant protein A magnetic bead can realize rapid purification of immunoglobulin, saving about 80% of treatment time and reducing total purification costs by 50%. In addition, the alkali-resistant protein A magnetic bead has high alkali resistance. An alkaline method for in situ cleaning can be performed to regenerate the magnetic bead after use. The magnetic bead has rapid magnetic response and good dispersiveness, realizing rapid magnetic bead enrichment, cleaning, and elution.

(Continued)

The magnetic bead facilitates automated, high-throughput, and large volume purification of a sample.

20 Claims, 2 Drawing Sheets

Specification includes a Sequence Listing.

(51) Int. Cl.
  *B01J 20/10* (2006.01)
  *B01J 20/28* (2006.01)
  *B01J 20/34* (2006.01)
  *B03C 1/01* (2006.01)
  *C07K 1/14* (2006.01)
  *C07K 16/00* (2006.01)

(52) U.S. Cl.
  CPC ... *B01J 20/28004* (2013.01); *B01J 20/28007* (2013.01); *B01J 20/28009* (2013.01); *B01J 20/3425* (2013.01); *B03C 1/01* (2013.01); *C07K 1/14* (2013.01); *C07K 16/00* (2013.01)

(56) References Cited

FOREIGN PATENT DOCUMENTS

| CN | 103483602 | A |   | 1/2014 |         |
|----|-----------|---|---|--------|---------|
| CN | 103483626 | A |   | 1/2014 |         |
| CN | 104059133 | A | * | 9/2014 | C07K 1/22 |
| CN | 104059133 | A |   | 9/2014 |         |
| CN | 104475041 | A |   | 4/2015 |         |
| JP | 2014-207905 | A |   | 11/2014 |       |
| WO | WO 2005/076938 | A2 |   | 8/2005 |     |
| WO | WO 2006/112771 | A1 |   | 10/2006 |    |
| WO | WO 2007/050017 | A1 |   | 5/2007 |     |
| WO | WO 2016/104338 | A1 |   | 6/2016 |     |

OTHER PUBLICATIONS

Landfester et al. (J. Phys.: Condens. Matter, 2003, 15, S1345-S1361). (Year: 2003).*

Jinggang et al., "$Fe_3O_4$ Magnetic Dextran Nanoparticles Modified with SPA Ligand for IgG Purification," *Biotechnology Bulletin* 7:201-208, 2014.

Ma and Li, "Preparation of Sepharose-SPA Immunomagnetic Microspheres and Its Application in IgG Separation," *Journal of Xihua University* 29:181-186, 2010.

International Search Report and Written Opinion dated Mar. 29, 2018 for PCT/CN2018/071397, with English translation of ISR (12 pages).

Holschuh and Schwämmle, "Preparative purification of antibodies with protein A—an alternative to conventional chromatography," *J Magn Magn Mater.* 293:345-348, 2005.

* cited by examiner

M: Marker (M00516)
1: Stock solution 2μl
2: Supernatant 2μl
3: Washing 8μl
4: Elution 5μl

SEQUENCE LISTING

<160> NUMBER OF SEQ ID NOS: 2

<210> SEQ ID NO 1
<211> LENGTH: 58
<212> TYPE: PRT
<213> ORGANISM: Artificial Sequence
<220> FEATURE:
<223> OTHER INFORMATION: amino acid sequence 1 of alkali-resistant protein A

<400> SEQUENCE: 1

Ala Asp Gly Lys Phe Glu Lys Glu Gln Gln Asn Ala Phe Tyr Glu Ile
1               5                   10                  15

Leu His Leu Pro Asn Leu Thr Glu Glu Gln Arg Asn Ala Phe Ile Gln
            20                  25                  30

```
Ser Leu Lys Asp Asp Pro Ser Gln Ser Thr Asn Val Leu Gly Glu Ala
        35                  40                  45

Lys Lys Leu Asn Asp Ala Gln Ala Pro Lys
    50                  55

<210> SEQ ID NO 2
<211> LENGTH: 58
<212> TYPE: PRT
<213> ORGANISM: Artificial Sequence
<220> FEATURE:
<223> OTHER INFORMATION: amino acid sequence 2 of alkali-resistant
      protein A

<400> SEQUENCE: 2

Ala Asp Gly Lys Phe Glu Lys Glu Gln Gln Asn Ala Phe Tyr Glu Ile
1               5                   10                  15

Leu His Leu Pro Asn Leu Thr Glu Glu Gln Arg Asn Ala Phe Ile Lys
                20                  25                  30

Ser Ile Arg Asp Pro Ser Gln Ser Thr Asn Val Leu Gly Glu Ala
        35                  40                  45

Lys Lys Leu Asn Asp Ala Gln Ala Pro Lys
    50                  55
```

HIGH-LOADING AND ALKALI-RESISTANT PROTEIN A MAGNETIC BEAD AND METHOD OF USE THEREOF

FIELD

The present invention relates to an alkali-resistant magnetic bead, and particularly to a high-loading and alkali-resistant protein A magnetic bead. The present invention also relates to a method for purifying an antibody using the alkali-resistant protein A magnetic bead.

BACKGROUND

Biotechnology is one of the fastest growing areas of high technology in the world today. As one of the fields of biotechnology, antibody drugs have achieved remarkable market performance in recent years. Antibody drugs have been widely used in basic biomedical research and diagnosis and treatment of diseases (such as cancer, organ transplant rejection, autoimmune diseases, etc.). Many pharmaceutical companies, especially biotechnology pharmaceutical companies, have gradually entered the field of development and production of antibody drugs. With the emergence of a great number of therapeutic pharmaceutical antibodies in the medical field, accelerating the research and development process and optimizing the production process are getting more and more attention.

In general, two important processes in the development of new antibodies require purification techniques: 1) early high-throughput screening of antibodies and 2) large-scale production of antibodies.

Immunized animals are subjected to antigen immunization to generate polyclonal antibodies. These antibody-producing cells require subsequent processing and screening to obtain effective monoclonal antibody cells. In this session, a large number of antibody cell screening work will be involved. A conventional screening method involves culturing a small amount of monoclonal cells (5-50 mL), purifying the cells by using an affinity resin, harvesting an antibody from the cell culture, and then testing the effect of the antibody. The purification process is cumbersome, including sample centrifugation and filtration, column packing with the resin, loading, washing and elution, etc. Usually, one sample corresponds to one column, which is difficult to achieve high-throughput and large-scale purification. Purification of antibodies with magnetic beads can avoid the cumbersome processing steps of sample centrifugation and filtration, column packing, etc. Using a fast magnetic response process to efficiently complete the processes of loading and incubation, washing and elution, etc., in combination with an automated apparatus, can simultaneously process up to 96 samples, thereby achieving fast and high-throughput screening. In the conventional large-scale production of antibodies, purification is carried out by means of a purification resin. The same problems may be encountered when purifying a large-volume sample with the resin: complicated processes including sample centrifugation and filtration, and column packing with a packing material, and a lot of time and manpower required for loading, washing and elution due to the restriction of the flow rate through the column.

High-throughput and large-scale purification of antibodies can be generally achieved quickly and easily using magnetic beads. However, commercially available magnetic beads are poor in static loading, magnetic response and dispersiveness, and are mainly used for enrichment of a small volume of micro-samples, which cannot meet the large-scale purification application of antibodies or proteins. The dynamic loading of traditional resins is generally 35-45 mg/mL, and in order to prevent sample loss, the actual sample-loading amount is controlled to be between 60%-80% of the dynamic loading of the resins, corresponding to the actual used loading of between 20-36 mg/mL. The current commercially available magnetic beads have a static loading of at most 35 mg/mL. To achieve the same purification ability as the resins, the amount of magnetic beads required is basically equivalent to the amount of the resins used. The production cost of magnetic beads is often 2-3 times that of the resins, so that the magnetic beads do not have raw material cost advantage in purification. The alkali-resistant protein A magnetic bead of the present invention has a binding loading greater than 50 mg/ml. With the magnetic bead of the present invention, the relative cost advantage is effectively increased while high-throughput and large-scale purification of antibodies is quickly and easily realized.

Antibodies are produced from cell culture. Antibodies of interest are produced in cells or secreted into the surrounding medium. In the process of culturing cells, the addition of cofactors such as sugars, amino acids, and growth factors to the culture medium is required, so it is necessary to separate the antibody from other cellular components in the culture medium to a sufficient purity before it can be used as a therapeutic agent for humans. The most commonly used method of antibody purification is affinity chromatography, which has the advantages of being simple, rapid and highly selective, and can significantly reduce the subsequent purification steps. Maintaining low production costs in modern industry is also an important requirement in the production process. If the purification chromatography medium required for production can be used repeatedly, the production cost of the antibody can be significantly reduced. However, since non-eluted proteins, protein aggregates, and even substances harmful to the human body, such as viruses and endotoxins, may be left each time the antibody is purified using the chromatography medium, the chromatography medium must be cleaned when it is reused. The most effective way to recover the chromatography medium now is an alkaline process called in situ cleaning. The standard procedure of this method involves treating the purification medium with 0.5 M sodium hydroxide (NaOH). This harsh way can effectively remove impurities, but it is likely to damage the purification medium. The ligand of the alkali-resistant protein A magnetic bead of the present invention is a highly alkali-resistant Protein A, which can withstand a highly alkaline environment of pH 12-14. Therefore, using the magnetic bead of the present invention enables an alkaline in situ cleaning mode, effectively removes impurities, restores high-loading binding characteristics of the magnetic bead, and achieves the effect of up to 50 or more times of repeated uses.

SUMMARY

In one aspect, the present invention provides a high-loading and alkali-resistant protein A magnetic bead. The magnetic bead can maintain chemical stability under pH 2-14 and has an immunoglobulin IgG binding capacity greater than 50 mg/mL.

In one embodiment, the high-loading and alkali-resistant protein A magnetic bead has an immunoglobulin IgG binding capacity greater than 40 mg/mL after in situ cleaning in an alkaline solution at pH 10-14 for more than 50 times each for 15 min.

In one embodiment, the high-loading and alkali-resistant protein A magnetic bead has a specific saturation magnetization greater than 60 eum/g.

In one embodiment, the high-loading and alkali-resistant protein A magnetic bead has a particle size ranging from 20 nm to 200 nm or from 30 µm to 200 µm.

In one embodiment, the high-loading and alkali-resistant protein A magnetic bead comprises a magnetic core portion and a ligand portion, wherein the main component of the magnetic core portion is $Fe_3O_4$, and the ligand portion is an alkali-resistant protein A. Preferably, the magnetic core portion also comprises $Fe_2O_3$, wherein the mass ratio of $Fe_2O_3:Fe_3O_4$ is 1:1 to 1:100.

In one embodiment, the amount of the alkali-resistant protein A on the high-loading and alkali-resistant protein A magnetic bead is greater than or equal to 3 mg/mL.

In one embodiment, the magnetic core portion of the high-loading and alkali-resistant protein A magnetic bead is superparamagnetic.

In one embodiment, the magnetic core portion is coated with a coating layer composed of an inorganic or organic material selected from one or more of silica, glucan, agarose, polystyrene, polyglycidyl methacrylate, polyhydroxyethyl methacrylate, polystyrene-glycidyl methacrylate, and combinations thereof, and the ligand portion is coupled to the coating layer.

In one embodiment, the coating layer has a reactive group required for crosslinking with the ligand, or a reactive group required for crosslinking with the ligand by chemical activation on the surface of the coating layer or by means of coupling. Preferably, the reactive group is selected from hydroxyl, carboxyl, amino and epoxy groups. Preferably, the agarose is crosslinked agarose.

In one embodiment, the alkali-resistant protein A can maintain stability of the advanced protein structure in a strong alkali environment at pH 10-14, so as to ensure the ability of binding to immunoglobulin IgG after being treated under harsh alkaline conditions.

In one embodiment, the alkali-resistant protein A magnetic bead contains 2-4 domains that can bind to immunoglobulin IgG.

In one embodiment, the alkali-resistant protein A is bound to the coating layer by coupling with the agarose.

In one specific embodiment, the alkali-resistant protein A comprises an amino acid sequence of SEQ ID NO: 1 or an amino acid sequence of SEQ ID NO: 2, or both of amino acid sequences of SEQ ID NO: 1 and SEQ ID NO: 2.

In one specific embodiment, the alkali-resistant protein A is a homologous 2-4-mer and/or heterologous 2-4-mer covalently formed by the aforementioned amino acid sequence, preferably a dimer, which may be a homodimer and/or a heterodimer.

In another aspect, the present application also provides a method for purifying and/or detecting an immunoglobulin, the method comprising a step of contacting a sample containing the immunoglobulin with the aforementioned high-loading and alkali-resistant protein A magnetic bead.

In another aspect, the present application also provides a method for regenerating the high-loading and alkali-resistant protein A magnetic bead, the method comprising: soaking the high-loading and alkali-resistant protein A magnetic bead in 0.1 to 0.5 M sodium hydroxide solution or potassium hydroxide solution or a mixed solution of both for 0.1 to 1 h, then soaking the magnetic bead with pure water or a buffer or rinsing the magnetic bead for 3 to 5 times to completely remove the alkaline solution, and storing the high-loading and alkali-resistant protein A magnetic bead in an equilibration buffer.

The alkali-resistant protein A magnetic bead according to the present application has a static loading greater than 50 mg/mL. By using the alkali-resistant protein A magnetic bead of the present invention, about 80% of treatment time can be saved and total purification costs can be reduced by 50%. In addition, the alkali-resistant protein A magnetic bead according to the present application has high alkali resistance, rapid magnetic response and good dispersiveness, realizing rapid magnetic bead enrichment, cleaning, and elution, and facilitating automated, high-throughput, and large volume purification of a sample.

Additionally, since the alkali-resistant protein A magnetic bead according to the present application has alkali resistance, an alkaline method for in situ cleaning can be performed to regenerate the magnetic bead after use.

DETAILED DESCRIPTION OF THE INVENTION

Figure 1:
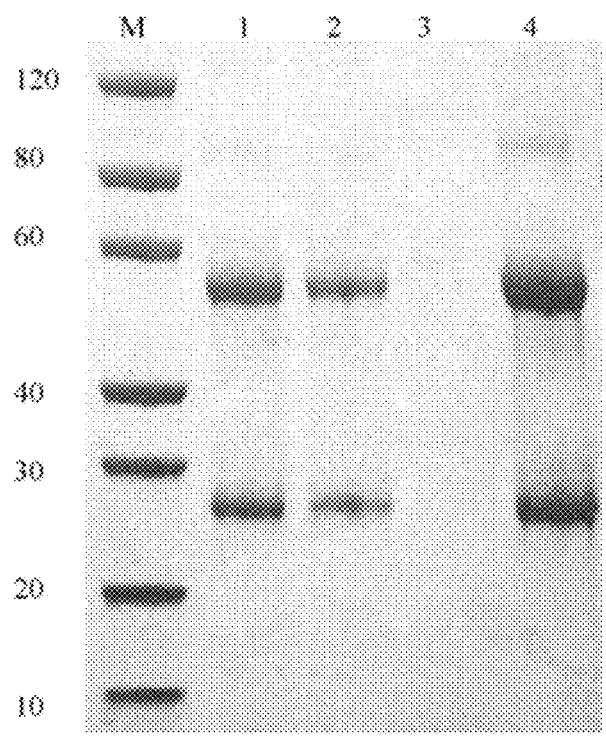
FIG. 1 is a gel electrophoresis photograph showing the effect of the alkali-resistant protein A magnetic bead of the present invention for purification of an immunoglobulin. Loaded samples on lanes 1, 2, 3, and 4 are a sample solution before purification (stock solution), a sample solution after adsorption by the alkali-resistant protein A magnetic bead (supernatant), a washing buffer after cleaning the alkali-resistant protein A magnetic bead (washing), and an elution buffer after cleaning the alkali-resistant protein A magnetic bead (elution), respectively. M: molecular weight Marker.

As used herein, the term "alkali-resistant protein A" refers to a protein A that has been artificially altered in amino acid sequence such that it retains its tertiary structure in high alkaline conditions (e.g., pH 10-14), thereby retaining IgG binding activity.

As used herein, the term "alkali-resistant protein A magnetic bead" refers to a magnetic bead that binds to the above-mentioned alkali-resistant protein A on its surface. The alkali-resistant protein A is generally bound to the magnetic bead by a coating layer (e.g., agarose) on a magnetic core.

As used herein, the term "static loading" refers to, when magnetic bead is in sufficient contact with a sample to be bound, the capacity of IgG antibody bound per unit amount of the magnetic bead. "High loading" means that the binding capacity is greater than 50 mg/mL.

As used herein, a "homodimer" of the alkali-resistant protein A refers to a dimer formed by the amino acid sequence 1 or the amino acid sequence 2 given below in the present application. A "heterodimer" refers to a dimer formed by the amino acid sequence 1 and the amino acid sequence 2 given below in the present application. The manner in which the dimer is formed includes linking the expressed fusion protein in tandem by a recombination method, and linking the synthesized amino acid sequence 1 and/or amino acid sequence 2 by a small molecule (e.g., a short peptide, an organic molecule), and so on.

The term "chemical stability" used in reference to an alkali-resistant magnetic bead A, means that the alkali-resistant magnetic bead A maintains its high static loading after in situ cleaning in an alkaline solution for multiple times. This chemical stability includes stability of the coating layer (e.g., agarose) and the alkali-resistant protein A of the magnetic bead, and the coupling between the alkali-resistant protein A and the coating layer.

The present invention is further illustrated by the following specific examples.

Example 1. Preparation of Magnetic Core

The magnetic bead mentioned in the present application is mainly composed of ferroferric oxide ($Fe_3O_4$), that is, the amount of ferroferric oxide is not less than 50%. The magnetic core can be prepared by a mechanical grinding method, a precipitation method (chemical coprecipitation, oxidation precipitation, reduction precipitation), a microemulsion method, a solvothermal method, a sol-gel method, thermal decomposition of organics, and other methods.

For example, the $Fe_3O_4$ magnetic core with a particle size of 10 nm-50 nm can be prepared by the conventional chemical coprecipitation method. Ferrous sulfate heptahydrate and ferric chloride hexahydrate were mixed in a molar ratio of 1:1 to 1:2 and dissolved in a 0.5-2 molar hydrochloric acid solution, and a 10-25% aqueous ammonia solution was slowly added thereto. During the addition of the aqueous ammonia, a stirring paddle was used to keep the solution in an agitated state, and the rotation speed of the stirring paddle was maintained between 100-500 rpm to ensure fast and uniform mixing. As the aqueous ammonia was continuously added, the pH of the solution gradually increased. When the pH reached 13, the addition of the aqueous ammonia was stopped and stirring was kept for 0.5-2 h. The soluble matter was removed by cleaning with pure water, and the precipitate was a magnetic core rich in $Fe_3O_4$.

A magnetic core with a larger particle size, such as a particle size of 30 μm to 200 μm, can be prepared by the solvothermal method. Specifically, $FeSO_4 \cdot 7H_2O$ and $Fe(NO_3)_3 \cdot 9H_2O$ of appropriate concentrations were mixed in a polyethylene beaker at a molar ratio of 1:1 to 1:2, appropriate amounts of urea and surfactant SDS were added thereto, and the mixture was uniformly stirred to obtain a clear solution. The solution was placed in a high-pressure reaction kettle, and an appropriate amount of water was added between an inner wall of the kettle body and the beaker to make the filling degree of 0.6. The nut was tightened, the reaction kettle was sealed, nitrogen gas was introduced (as a protective gas), and the system was purged for 30 min. The reaction kettle was heated to 125° C., the system pressure was maintained at about 5-7 atm, and the reaction was allowed to last for a period of time. The reaction product was filtered, washed, and dried to obtain a magnetic core having a larger particle size.

Example 2. Preparation of Silica-Coated Magnetic Bead

The magnetic core prepared in example 1 is superparamagnetic, that is, it is easy to magnetize under the action of an external magnetic field but has no hysteresis and has chemical stability under certain conditions. However, the magnetic core is easily oxidized to lose its superparamagnetism, and its dispersion in solution is poor. It needs to be coated with other materials to achieve the ability to block oxidation and tolerate strong acids and bases. This example describes that the magnetic core prepared in example 1 is coated with one or more layers of silica.

The silica coated magnetic bead can be prepared by the sodium silicate hydrolysis method: saturated silicic acid is prepared by using sodium silicate as a raw material, and silicic acid is further condensed into silica under acidic or alkaline conditions, which covered the surface of magnetic nanoparticles. Sodium silicate was added into a dispersion system of $Fe_3O_4$ magnetic particles, and HCl was slowly added dropwise to adjust the pH to about 6-10, so that one or more layers of silica covered the surface of the $Fe_3O_4$ magnetic core.

The silica coated magnetic bead can also be prepared by the ethyl orthosilicate hydrolysis method: an appropriate amount of $Fe_3O_4$ nanoparticles were weighed and dispersed in absolute ethanol, a few drops of oleic acid were added dropwise thereto, and then the mixture was ultrasonically dispersed for 10 min. Then, the dispersed solution was transferred to a 250 mL three-necked flask, and ethyl orthosilicate $Si(OC_2H_5)_4$ (TEOS) and $NH_3 \cdot H_2O$ were added to the three-necked flask at a molar ratio of 1:2, and the solution was stirred to react for 3 h. After the reaction was completed, under the attraction of a magnetic field, washing was repeated using distilled water until the solution was clarified, and the resulting precipitate was dried under vacuum at 70° C. to finally obtain a silica/ferroferric oxide composite nanoparticle magnetic bead.

Example 3. Preparation of Agarose-Coated Magnetic Bead

The agarose coated magnetic bead is prepared by a reverse phase suspension method using cyclohexane, Span 80 (SP80) and double distilled water as an organic phase, an emulsifier and an aqueous phase, respectively.

400 mL of cyclohexane was added to a 1000 mL three-necked flask, heated in a water bath where the temperature of the water bath was adjusted to 60° C., and stirred evenly at 500 rpm. An appropriate amount of SP80 was added and stirring was continued for 30 min to 1 h. At the same time, an agarose solution was prepared. 150-200 mL of a 4%-6% agarose solution was prepared, and an appropriate amount of the silica coated magnetic bead prepared in example 2 was added and dissolved by heating in a microwave oven. After complete dissolution, it was immediately added to the cyclohexane solution, and stirred for 10 min with the rotation speed of the stirrer adjusted to 1400 rpm. Then, the temperature was lowered to 25° C. After stirring for another 15 min, the flask solution was transferred to a beaker, and under the action of magnet attraction, cleaning was performed with 95% absolute ethanol and double distilled water alternately for three times. Finally, the precipitate was recovered to obtain the agarose-coated magnetic bead.

Example 4. Surface Activation of Agarose-Coated Magnetic Bead

In order to enable other ligands such as an alkali-resistant protein A to be bound on the surface of the magnetic bead prepared in example 3 by means of chemical coupling, it is necessary to chemically activate the surface of the magnetic bead, for example, by epoxy activation of the hydroxyl groups on the surface of the magnetic bead to achieve coupling with the ligand. 100 mL of the agarose-coated magnetic bead was added to a 1 L conical flask, and a 1 M NaOH solution was prepared at the same time. The 1 M NaOH solution was added to the conical flask at a volume ratio of the agarose coated magnetic bead to the NaOH solution of 1:1 to 1:1.5, and the mixture was shaken evenly. Finally, an appropriate amount of epichlorohydrin was added to the 1 L conical flask, and the conical flask was placed in a shaking incubator, the temperature was adjusted to 37° C., and the reaction lasted for 1-1.5 h. At the end of the reaction, the surface-activated agarose bead could be obtained.

The ligand moiety could be coupled through a variety of reactive groups. For example, epichlorohydrin, sodium hydroxide and sodium borohydride (NaBH$_4$) were incubated with the agarose coated magnetic bead at a certain temperature on a thermostatic shaker, thereby providing the epoxy reactive groups required for coupling. Chemical activation reaction with the agarose microsphere was performed by other means in addition to epichlorohydrin, including but not limited to, allyl glycidyl ether, cyanogen bromide, N-hydroxysuccinimide (NHS), dimethyl diheptadine dihydrochloride (DMP), etc., thereby providing reactive groups such as carboxyl and amino groups required for coupling.

Example 5. Coupling of Surface-Activated Magnetic Bead and Protein A

The alkali-resistant protein A could be covalently coupled to the activated agarose magnetic bead via amino, carboxyl, hydroxyl or sulfhydryl groups. For example, an agarose magnetic bead containing the alkali-resistant protein A could be prepared by bonding an amino acid having a nitrogen-containing group in the alkali-resistant protein A to the surface of the epoxy-activated agarose.

For coupling about 10 mg of the alkali-resistant protein A to the surface of 1 mL of the activated agarose magnetic bead via epoxy group, 100 mL of the activated agarose magnetic bead was added to a 1 L conical flask. The magnetic bead was cleaned 4-5 times with double distilled water by means of magnet adsorption. An alkali-resistant protein A solution was prepared at a concentration of 10-12 mg/mL, pH of 8.5-9.5. 100 mL of the prepared alkali-resistant protein A solution was added into a 1 L conical flask, and the conical flask was placed in a full-temperature shaking incubator where the temperature was adjusted to 28° C. After 24 h at 120 rpm, the magnetic bead was cleaned 4-5 times using double-distilled water by means of magnet adsorption, to obtain a precipitate, the alkali-resistant protein A magnetic bead.

The resulting magnetic bead was stored as a 25% suspension in 20% ethanol in a total volume of 4 mL.

In this example, an alkali-resistant protein A dimer prepared by the present inventors was used as a coupling ligand to be coupled with the activated agarose magnetic bead to prepare a high-loading and alkali-resistant protein A magnetic bead. The characteristic sequence of the alkali-resistant protein A is as follows:

```
amino acid sequence 1 of alkali-resistant proteinA (SEQ ID NO: 1):
Ala Asp Gly Lys Phe Glu Lys Glu Gln Gln Asn Ala Phe Tyr Glu
 1               5                  10                  15

Ile Leu His Leu Pro Asn Leu Thr Glu Glu Gln Arg Asn Ala Phe
                20                  25                  30

Ile Gln Ser Leu Lys Asp Asp Pro Ser Gln Ser Thr Asn Val Leu
                35                  40                  45

Gly Glu Ala Lys Lys Leu Asn Asp Ala Gln Ala Pro Lys
                50                  55          58 amino acid sequence 2 of alkali-resistant proteinA (SEQ ID NO: 2):
Ala Asp Gly Lys Phe Glu Lys Glu Gln Gln Asn Ala Phe Tyr Glu
 1               5                  10                  15

Ile Leu His Leu Pro Asn Leu Thr Glu Glu Gln Arg Asn Ala Phe
                20                  25                  30

Ile Lys Ser Ile Arg Asp Asp Pro Ser Gln Ser Thr Asn Val Leu
                35                  40                  45

Gly Glu Ala Lys Lys Leu Asn Asp Ala Gln Ala Pro Lys
                50                  55          58
```

Using a homodimer or heterodimer of the protein A having the sequence 1 or sequence 2 above as a ligand, the amount of the alkali-resistant protein A bound to the alkali-resistant protein A magnetic bead prepared in this example is greater than or equal to 3 mg/mL, so that a high ability to bind to immunoglobulin IgG (>50 mg/mL) is obtained.

Example 6. Purification of Immunoglobulin with the Agarose Magnetic Bead Coupled with the Alkali-Resistant Protein A The high-loading and alkali-resistant protein A agarose magnetic bead prepared in example 5 was tested. The above magnetic bead was uniformly mixed, 0.4 mL was placed in a 15 mL centrifuge tube, and a magnet (natural permanent magnet or electromagnet) was used to adsorb the magnetic bead on the inside of the tube wall for about 30-60 sec. The supernatant was poured off or removed with a pipette. The magnet was removed, 2 mL of double distilled water was added to the tube and thoroughly mixed to clean the bead. The magnetic bead was adsorbed by a magnet to settle on the inside of the tube wall, and the adsorption time was about 30-60 sec. The supernatant was poured off or removed with a pipette. This process was repeated 2-3 times to remove residual ethanol. Similarly, the magnetic bead was cleaned 2-3 times with 10 ml of 20 mM phosphate buffer, and the buffer was removed.

10 mL of Human serum immunoglobulin at a concentration of 1 mg/mL was used as a test sample, and the sample was added to the above 15 mL centrifuge tube. The tube was covered and sealed with parafilm to prevent sample spillage. The tube was incubated on a rotating and mixing rack for 1-4 h. The magnetic bead was adsorbed by a magnet to settle on the inside of the tube wall, and the adsorption time was about 60-90 sec. The supernatant was poured off or removed with a pipette. Similarly, the bead was cleaned 2-3 times with 10 mL of 20 mM phosphate buffer to remove the unadsorbed sample and impurities. The protein of interest was eluted with 500 µL of a 0.1 M glycine elution solution (pH 3.0) three times, and then detected by SDS-PAGE at 4-20% gel concentration. As shown in FIG. 1, the alkali-resistant protein A magnetic bead can separate a high-purity immunoglobulin. The static loading of the alkali-resistant protein A magnetic bead is measured to be up to 65 mg/mL. The static loadings of commercially available agarose magnetic beads are all less than 30 mg/mL (Table 1).

TABLE 1

Comparison of static loading of agarose magnetic beads from different companies

| Agarose magnetic bead | Supplier | Static binding loading (mg/mL) |
|---|---|---|
| Protein A | GE | 27 |
| | Promega | 18 |
| | Beaver | 25-30 |
| | The present application | >50 |

Example 7. Comparison of Binding Ability of Protein A Magnetic Beads Having Different Numbers of Binding Domains A protein A containing two domains bound to immunoglobulin IgG and a protein A containing five domains bound to immunoglobulin IgG were respectively coupled to the agarose magnetic bead by the above coupling method. Each 100 µl of the precipitated magnetic bead was taken, and thoroughly mixed with 2 mL of double distilled water to clean the magnetic bead. 2 mL of 5 mg/mL human IgG (hIgG) was dissolved in 20 mM PBS and incubated with the previously cleaned magnetic bead for 1 h at room temperature. Then, the magnetic bead was adsorbed by a magnet to settle on the inside of the tube wall, and the supernatant was removed. The magnetic bead was cleaned 2-3 times with 10 mL of 20 mM phosphate buffer to remove the unadsorbed sample and impurities. Finally, the protein of interest was eluted with 500 µL of a 0.1 M glycine elution solution (pH 3.0) three times. The amount of hIgG in each eluent was measured to derive the static binding loading per unit volume of the magnetic bead. The results are shown in the table below: the loading of the protein A magnetic bead containing two domains is higher than that of the protein A magnetic bead containing five domains.

TABLE 2

Comparison of binding ability of protein A magnetic beads having different numbers of binding domains

| Name | First elution (500 µl) | Second elution (500 µl) | Third elution (500 µl) | Static binding loading (mg hIgG/ml) |
|---|---|---|---|---|
| 5-Domain protein A magnetic bead | 6.84 | 1.181 | 0.181 | 40.93 |
| 2-Domain protein A magnetic bead | 11.189 | 1.729 | 0.228 | 65.73 |

Example 8. Alkali Resistance Test of the Alkali-Resistant Protein A Magnetic Bead The alkali-resistant protein A agarose magnetic bead prepared in example 5 above was tested by in situ cleaning in an alkaline solution. Purification of the immunoglobulin was first carried out in accordance with the procedure of example 6. After the immunoglobulin was eluted with 0.1 M pH 3.0 glycine eluent, the magnetic bead was soaked in 5 mL of a 0.5 M NaOH solution as the alkaline solution for in situ cleaning for 15 min, and then cleaned and balanced using 10 mL of 20 mM phosphate buffer (containing 0.15 M NaCl, 30 mM $Na_2HPO_4$, 10 mM $NaH_2PO_4$, pH 7.0) three times, to complete one test cycle of in situ cleaning in the alkaline solution. The immunoglobulin binding ability of the alkali-resistant protein A magnetic bead can be determined in each cycle based on the immunoglobulin amount in the eluent.

Figure 2:
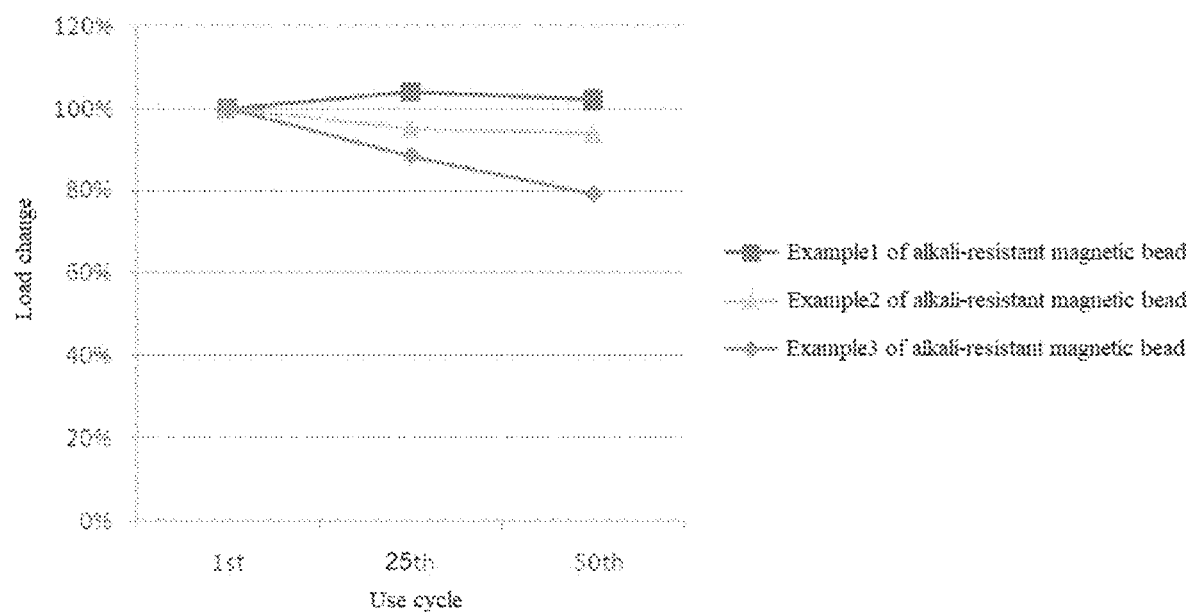
FIG. 2 is a graph showing the change of loading of the magnetic bead of the present invention after being cleaned with an alkaline solution for multiple times. Alkali-resistant magnetic bead examples 1, 2, and 3 are three independently prepared alkali-resistant protein A magnetic beads, respectively.

As shown in FIG. 2, after 50 test cycles by in situ cleaning in the alkaline solution, the alkali-resistant protein A magnetic bead as a ligand still maintains good immunoglobulin binding ability.

The invention claimed is:

1. A high-loading and alkali-resistant protein A magnetic bead, comprising:
   a magnetic core portion comprising $Fe_3O_4$; and
   a ligand portion comprising an alkali-resistant protein A, wherein the alkali-resistant protein A comprises the amino acid sequence of SEQ ID NO: 1, the amino acid sequence of SEQ ID NO: 2, a homologous 2-4-mer formed by the sequence of SEQ ID NO: 1 or the sequence of SEQ ID NO: 2, and/or a heterologous 2-4-mer formed by the sequence of SEQ ID NO:1 and the sequence of SEQ ID NO: 2, and retains its tertiary structure in high alkaline conditions of pH 10-14,
   wherein the magnetic bead can maintain chemical stability under pH 2-14, has an immunoglobulin IgG binding capacity greater than 50 mg/mL, and has a particle size ranging from 30 μm to 200 μm.

2. The high-loading and alkali-resistant protein A magnetic bead of claim 1, wherein the magnetic bead has an immunoglobulin IgG binding capacity greater than 40 mg/mL after in situ cleaning in an alkaline solution at pH 10-14 for more than 50 times each for 15 min.

3. The high-loading and alkali-resistant protein A magnetic bead of claim 1, wherein the alkali-resistant protein A comprises a homodimer formed by the sequence of SEQ ID NO: 1 or the sequence of SEQ ID NO: 2.

4. The high-loading and alkali-resistant protein A magnetic bead of claim 1, wherein the alkali-resistant protein A comprises a heterodimer formed by the sequence of SEQ ID NO: 1 and the sequence of SEQ ID NO: 2.

5. The high-loading and alkali-resistant protein A magnetic bead of claim 1, wherein the magnetic core portion further comprises $Fe_2O_3$, wherein the mass ratio of $Fe_2O_3$:$Fe_3O_4$ is 1:1 to 1:100.

6. The high-loading and alkali-resistant protein A magnetic bead of claim 1, wherein the amount of the alkali-resistant protein A on the high-loading and alkali-resistant protein A magnetic bead is greater than or equal to 3 mg/mL.

7. The high-loading and alkali-resistant protein A magnetic bead of claim 1, wherein the magnetic core portion is superparamagnetic.

8. The high-loading and alkali-resistant protein A magnetic bead of claim 1, wherein the magnetic core portion is coated with a coating layer composed of an inorganic or organic material selected from one or more of silica, glucan, agarose, polystyrene, polyglycidyl methacrylate, polyhydroxyethyl methacrylate, polystyrene-glycidyl methacrylate, and combinations thereof, and the ligand portion is coupled to the coating layer.

9. The high-loading and alkali-resistant protein A magnetic bead of claim 8, wherein the coating layer has a reactive group required for crosslinking with the ligand, or a reactive group required for crosslinking with the ligand by chemical activation on the surface of the coating layer or by means of coupling.

10. The high-loading and alkali-resistant protein A magnetic bead of claim 9, wherein the reactive group is selected from hydroxyl, carboxyl, amino and epoxy groups.

11. The high-loading and alkali-resistant protein A magnetic bead of claim 8, wherein the alkali-resistant protein A is bound to the coating layer by coupling with the agarose.

12. The high-loading and alkali-resistant protein A magnetic bead of claim 1, wherein the alkali-resistant protein A contains 2-4 domains that can bind to immunoglobulin IgG.

13. The high-loading and alkali-resistant protein A magnetic bead of claim 1, wherein the alkali-resistant protein A comprises the amino acid sequence of SEQ ID NO: 1.

14. The high-loading and alkali-resistant protein A magnetic bead of claim 1, wherein the alkali-resistant protein A is in the form of a recombinantly expressed fusion protein.

15. The high-loading and alkali-resistant protein A magnetic bead of claim 1, wherein the alkali-resistant protein A comprises the amino acid sequence of SEQ ID NO: 2.

16. The high-loading and alkali-resistant protein A magnetic bead of claim 1, wherein the alkali-resistant protein A comprises a homologous 2-4-mer formed by the sequence of SEQ ID NO: 1 or the sequence of SEQ ID NO: 2.

17. The high-loading and alkali-resistant protein A magnetic bead of claim 1, wherein the alkali-resistant protein A comprises a heterologous 2-4-mer formed by the sequence of SEQ ID NO:1 and the sequence of SEQ ID NO: 2.

18. A method for purifying and/or detecting an immunoglobulin, comprising a step of contacting a sample containing the immunoglobulin with the high-loading and alkali-resistant protein A magnetic bead of claim 1.

19. The method for purifying and/or detecting an immunoglobulin of claim 18, wherein the magnetic bead has an immunoglobulin IgG binding capacity greater than 40 mg/mL after in situ cleaning in an alkaline solution at pH 10-14 for more than 50 times each for 15 min.

20. A method for regenerating the high-loading and alkali-resistant protein A magnetic bead of claim 1, comprising: soaking the high-loading and alkali-resistant protein A magnetic bead in 0.1 M to 0.5 M sodium hydroxide solution or potassium hydroxide solution or a mixed solution of both for 0.1 to 1 h, then soaking the magnetic bead with pure water or a buffer or rinsing the magnetic bead for 3 to 5 times to completely remove the alkaline solution, and storing the high-loading and alkali-resistant protein A magnetic bead in an equilibration buffer.

\* \* \* \* \*